United States Patent [19]

Demerson et al.

[11] Patent Number: 4,515,961
[45] Date of Patent: May 7, 1985

[54] RESOLUTION OF (±)-1,8-DIETHYL-1,3,4,9-TETRAHYDROPYRANO[3,4,-B] INDOLE-1-ACETIC ACID USING ENRICHMENT CRYSTALLIZATION

[75] Inventors: Christopher A. Demerson, Montreal; Leslie G. Humber, Dollard-des-Ormeaux, both of Canada

[73] Assignee: American Home Products Corporation, New York, N.Y.

[21] Appl. No.: 523,986

[22] Filed: Aug. 16, 1983

[51] Int. Cl.$^3$ ............................................ C07D 498/04
[52] U.S. Cl. ..................................................... 548/432
[58] Field of Search ........................................ 548/432

[56] References Cited

U.S. PATENT DOCUMENTS 3,939,178  2/1976  Demerson et al. ............... 425/274
4,088,814  5/1978  McLoughlin et al. ............. 544/174

FOREIGN PATENT DOCUMENTS 59-0650  4/1984  Japan .

OTHER PUBLICATIONS

Demerson et al., J. Med. Chem., 18, 189 (1975).

Primary Examiner—Donald G. Daus
Assistant Examiner—Cecilia Shen

[57] ABSTRACT

Racemic (±)-1,8-diethyl-1,3,4,9-tetrahydroprano[3,4-b]indole-1-acetic acid is resolved using enrichment crystallization to obtain directly the (+)-enantiomer.

3 Claims, No Drawings

RESOLUTION OF (±)-1,8-DIETHYL-1,3,4,9-TETRAHYDROPYRANO[3,4,-B] INDOLE-1-ACETIC ACID USING ENRICHMENT CRYSTALLIZATION

BACKGROUND OF THE INVENTION

This invention relates to a process for resolving (±)-1,8-diethyl-1,3,4,9-tetrahydropyrano[3,4-b]indole-1-acetic acid using enrichment crystallization to obtain the corresponding (+)-enantiomer.

(±)-1,8-Diethyl-1,3,4,9-tetrahydropyrano[3,4-b]indole-1-acetic acid, an optically inactive racemic mixture, is known generically as etodolic acid or etodolac and is well known as an anti-inflammatory and analgesic agent, C. A. Demerson et al., U.S. Pat. No. 3,939,178, issued Feb. 17, 1976; and C. A. Demerson et al., J. Med. Chem., 18, 189 (1975) and 19, 391 (1976).

The resolution of racemic organic acids is unpredictable. Attempts to resolve etodolac have been plagued with numerous problems, for example, crystallization of the wrong enantiomer, selection of an appropriate base for forming the diastereoisomeric salt, low yields, multiple crystallizations and time consumption.

The herein described process avoids the above problems and the (+)-enantiomer is obtained directly and in a commercially feasible operation.

DESCRIPTION OF THE INVENTION

The process for preparing (+)-1,8-diethyl-1,3,4,9-tetrahydropyrano[3,4-b]indole-1-acetic acid comprises: allowing a solution containing an enantiomeric mixture of (+)- and (−)-1,8-diethyl-1,3,4,9-tetrahydropyrano[3,4-b]indole-1-acetic acid having at least 70 percent of (+)-1,8-diethyl-1,3,4,9-tetrahydropyrano[3,4-b]indole-1-acetic acid to crystallize, and collecting substantially pure (+)-1,8-diethyl-1,3,4,9-tetrahydropyrano[3,4-b]indole-1-acetic acid.

If required, the substantially pure (+)-1,8-diethyl-1,3,4,9-tetrahydropyrano[3,4-b]indole-1-acetic acid can be recrystallized to increase the enantiomeric purity of the (+)-enantiomer.

A preferred solvent for the crystallization is a mixture of benzene and petroleum ether, or a mixture of toluene and petroleum ether.

Preferably the solution containing the racemic mixture is allowed to crystallize for about one to four hours.

A preferred process for preparing (+)-1,8-diethyl-1,3,4,9-tetrahydropyrano[3,4-b]indole-1-acetic acid, comprises dissolving one part by weight of an enantiomeric mixtue of (+)- and (−)-1,8-diethyl-1,3,4,9-tetrahydropyrano[3,4-b]indole-1-acetic acid having at least 70 percent of (+)-1,8-diethyl-1,3,4,9-tetrahydropyrano[3,4-b]indole-1-acetic acid in about 4 to 5 parts by weight of toluene or benzene at about 50° to 100° C.; adding about 6 to 7 parts by weight of petroleum ether; seeding the solution with (+)-1,8-diethyl-1,3,4,9-tetrahydropyrano[3,4-b]indole-1-acetic acid; allowing the solution to crystallize for about two to four hours; and isolating substantially pure (+)-1,8-diethyl-1,3,4,9-tetrahydropyrano[3,4-b]indole-1-acetic acid.

The above mentioned enantiomeric mixture having at least 70% of the (+)-enantiomer is obtained by adding pure (+)-enantiomer to racemic etodolac. Racemic etodolac is a 1:1 (w/w) mixture of the (+)-enantiomer and the (−)-enantiomer.

An important feature of the present process is that the (+)-enantiomer is obtained substantially pure by direct crystallization so that further purification by recrystallization is not usually required. All these features avoid the expensive and tedious operations of purification procedures usually required for resolution and serve to promote the efficiency of the present process.

The anti-inflammatory and analgesic activity of (+)-1,8-diethyl-1,3,4,9-tetrahydropyrano[3,4-b]indole-1-acetic acid is determined by the methods described in the above cited U.S. Pat. No. 3,939,178. How to use and pharmaceutical formulations are also described in the patent. The useful anti-inflammatory and analgesic activity of the racemic mixture has been found to reside only in the (+)-enantiomer.

The following examples illustrate further this invention.

EXAMPLE 1

(+)-1,8-Diethyl-1,3,4,9-tetrahydropyrano[3,4-b]indole-1-acetic Acid

A mixture of (±)-1,8-diethyl-1,3,4,9-tetrahydropyrano[3,4-b]indole-1-acetic acid (5.0 g) and (+)-1,8-diethyl-1,3,4,9-tetrahydropyrano[3,4-b]indole-1-acetic acid (5.0 g) was dissolved in hot toluene (50 mL, containing 0.2% 2-t-butyl-4-methylphenol). The solution was diluted with petroleum ether (100 mL, bp 35°-60° C.) and then immediately seeded with (+)-1,8-diethyl-1,3,4,9-tetrahydropyrano[3,4-b]indole-1-acetic acid (0.005 g). After 3 hr of undisturbed crystallization, the resulting solid was filtered, washed wit 10 mL of cold toluene-petroleum ether (1:2), and dried to afford 7.43 g of the title compound (having enantiomeric purity of 92.5%). Recrystallization from hot toluene (35 mL) and petroleum ether (75 mL) over a 3 hr period as above, afforded 6.19 g of the title compound (having enantiomeric purity of 99.3%), mp 138°-140° C., and $[\alpha]_D +47.9°$ (c=1, isopropanol).

EXAMPLE 2

Effect on Primary Inflammation of Adjuvant Induced Arthritis

The method used was a modification of that described by J. Wax et al., J. Pharmac. Exp. Ther., 192, 166 (1975). Groups of rats were injected intradermally in the left hindpaw (injected hindpaw) with 0.1 mL of a fine suspension of killed and dried Mycobacterium butyricum (Difco) at a concentration of 5 mg/mL in liquid paraffin (Freund's complete adjuvant). Drugs were administered immediately before the adjuvant, 24 h and 48 h after the adjuvant (day 0, 1 and 2). The injected hindpaw volume was measured before the adjuvant and 24 after the last drug administration (day 3). The difference between the hindleg volume before the adjuvant injection and the day 3 reading represented the edema volume. Rats showing an inhibition of hindpaw edema of 25% or more when compared to the mean edema volume of the control group (10 rats) were considered to exhibit an anti-inflammatory effect. The dose which produced a positive effect in half the rats ($ED_{50}$) was calculated by probit analysis (D. J. Finney, Statistical Method in Biological Assay, MacMillan, New York, 1978). There were 10 to 20 rats per dose and 4 dose levels were used. An adjuvant-injected control group receiving water only was also included. Hindleg volume was determined by a mercury displacement method. Hindlegs were dipped in mercury up to the hairline and the amount displaced was read in grams on a direct reading balance. It represented the volume of the hindleg (13.6 g of mercury = 1 mL). Male Charles River albino rats weighing 180 to 200 g were used. The results are expressed $ED_{50}$'s, the dose which reduced, by 25% the edema of primary adjuvant arthritis in 50% of the rats. In this model the $ED_{50}$ for (+)-1,8-diethyl-1,3,4,9-tetrahydropyrano[3,4-b]indole-1-acetic acid was 0.7±0.3 mg/kg, while the (−)-enantiomer was inactive. The $ED_{50}$ of the (±)-racemate in this test was 1.1±0.5 mg/kg.

We claim:

1. A process for preparing (+)-1,8-diethyl-1,3,4,9-tetrahydropyrano[3,4-b]indole-1-acetic acid, which comprises allowing a solution of benzene-petroleum ether or toluene-petroleum ether containing an enantiomeric mixture of (+)-1,8-diethyl-1,3,4,9-tetrahydropyrano[3,4-b]indole]-acetic acid having at least 70 percent of (+)-1,8-diethyl-1,3,4,9-tetrahydropyrano[3,4-b]indole-1-acetic acid to crystallize, and collecting substantially pure (+)-1,8-diethyl-1,3,4,9-tetrahydropyrano[3,4-b]indole-1-acetic acid.

2. The process of claim 1 wherein the solution is allowed to crystallize for about one to four hours.

3. A process for preparing (+)-1,8-diethyl-1,3,4,9-tetrahydropyrano[3,4-b]indole-1-acetic acid, which comprises dissolving one part by weight of an enantiomeric mixture of (+)- and (−)-1,8-diethyl-1,3,4,9-tetrahydropyrano[3,4-b]indole-1-acetic acid having at least 70 percent of (+)-1,8-diethyl-1,3,4,9-tetrahydropyrano[3,4-b]indole-1-acetic acid in about 4 to 5 parts by weight of toluene or benzene at about 50° to 100° C.; adding about 6 to 7 parts by weight of petroleum ether; seeding the solution with (+)-1,8-diethyl-1,3,4,9-tetrahydropyrano[3,4-b]indole-1-acetic acid; allowing the solution to crystallize for about one to four hours; and isolating substantially pure (+)-1,8-diethyl-1,3,4,9-tetrahydropyrano[3,4-b]indole-1-acetic acid.

* * * * *